US006229051B1

(12) United States Patent
Sandefur

(10) Patent No.: US 6,229,051 B1
(45) Date of Patent: May 8, 2001

(54) CATALYST FOR OXIDATIVE NEF REACTION USING BASIC HYDROGEN PEROXIDE

(75) Inventor: Louise O. Sandefur, Batesville, AK (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/088,779

(22) Filed: Jun. 2, 1998

Related U.S. Application Data

(60) Provisional application No. 60/059,322, filed on Sep. 17, 1997, and provisional application No. 60/048,399, filed on Jun. 3, 1997.

(51) Int. Cl.[7] ........................ C07C 45/00; C07C 49/105
(52) U.S. Cl. ........................ 568/351; 568/367; 568/379
(58) Field of Search ........................ 568/351, 367, 568/379

(56) References Cited

U.S. PATENT DOCUMENTS

| | | | |
|---|---|---|---|
| 3,845,133 | * 10/1974 | Mordechai et al. | |
| 4,421,929 | * 12/1983 | Woo | 562/465 |
| 5,344,992 | 9/1994 | Drewes et al. | |
| 6,096,929 | * 8/2000 | Boaz | 568/316 |

FOREIGN PATENT DOCUMENTS

| | | |
|---|---|---|
| 714 046 | 9/1968 | (BE). |
| 224 589 | 7/1910 | (DE). |
| 1 618 442 | 12/1970 | (DE). |
| 0 470 856 A1 | 2/1992 | (EP). |
| 97/28122A | 8/1997 | (WO). |

OTHER PUBLICATIONS

Coombes et al., "On the Synthesis of 2–methylchromene–4–thione and 2–methyl–1–thiochromone", *Phosphorous and Sulfur,* vol. 14, No. 2, pp. 139–142 (1983).

Reid et al., "Addition of nitroalkanes to ortho–halo–nitrobenzenes. A new synthesis of 4–chloro–7–(trifluoromethyl)quinoline", *Tetrahedron Letters,* vol. 31, No. 8, pp. 1093–1096 (1990).

March, Jerry, "Advanced Organic Chemistry", John Wiley & Sons, Eds. New York, pp. 886–887 (1992).

Bartlett, et al., "A Mild, Oxidative Nitro–to Carbonyl Conversion and a New Prostaglandin Synthon", *Tetrahedron Letters,* No. 4, pp. 331–334 (1977).

Olah et al., "Synthetic Methods and Reactions; 89. Improved Transformation of Nitro Compounds into Carbonyl Compounds by Hydrogen Peroxide/Potassium Carbonate", *Synthesis,* pp. 662–663 (1980).

Reid et al., "Addition of Nitroalkanes to Ortho–Halo–Nitrobenzenes, A New Synthesis of 4–Chloro–7–(Trifluoromethyl) Quinoline", *Tetrahedron Letters,* vol. 31, No. 8, pp. 1093–1096 (1990).

Shechter et al., "An Effective General Method for Oxidizing Salts of Mononitro Compounds with Neutral Permanganate to Aldehydes and Ketones", *J. Org. Chem.,* vol. 27, pp. 3699–3701 (1962).

Pagano et al., "Oxidation of Nitronates with Persulfate and with Silver Ions", *J. Org. Chem.,* vol. 35, No. 2, pp. 295–303 (1970).

Bartlett et al., "A Mild, Oxidative Nitro–To–Carbonyl Conversion and a New Prostaglandin Synthon", *Tetrahedron Letters,* No. 4, pp. 331–334 (1977).

* cited by examiner

Primary Examiner—James O. Wilson
(74) Attorney, Agent, or Firm—Michael J. Blake, Esq.; Harry J. Gwinnell

(57) ABSTRACT

The preparation of carbonyl compounds by oxidizing a nitro functional group of an organic compound is described. Oxidation is accomplished under catalyzed oxidative Nef reaction conditions.

23 Claims, No Drawings

CATALYST FOR OXIDATIVE NEF REACTION USING BASIC HYDROGEN PEROXIDE

This application claims under 35 U.S.C. § 119(e) the benefit of U.S. Provisional Application No. 60/048,399, filed Jun. 3, 1997 and U.S. Provisional Application No. 60/059,322, filed Sep. 17, 1997, each of which is incorporated in its entirety by reference.

BACKGROUND OF THE INVENTION

1. Field of the Invention

The present invention relates to a process for the preparation of alkyl and aromatic ketones, aldehydes, or carboxylic acids. More preferably, the invention relates to a process for preparing aromatic ketones.

2. Description of the Related Art

Aromatic ketones are important synthetic intermediates for a number of valuable chemical compounds such as herbicides. Several such compounds are isoxazole and derivatives thereof (Cain et al., *Euro. Pat. App. EP* 470856 (1992)). These types of ketones are normally prepared by the Friedel-Crafts acylation of an aromatic nucleus. However, in some cases this methodology does not produce the desired isomer, and more indirect methods must be employed.

Conversion of nitro groups to the corresponding carbonyl can be achieved under Nef reaction conditions known in the art. For example, the preparation of aromatic ketones by an oxidative Nef reaction has been previously reported. Such aromatic ketones are shown to be useful as synthetic intermediates in the preparation of chemical pharmaceuticals. (Reid et al., *Tetrahedron Lett.* 31:1093 (1990)). Classic Nef reactions are performed by adding a solution of a nitronate anion to a strongly acidic aqueous solution. However, these conditions achieve only minimal conversion of the nitro group of a nitronate anion substituted on an aromatic ring to the corresponding ketone. Conversion to the desired ketone can be achieved under oxidative Nef reaction conditions. However, a large excess of hydrogen peroxide, which is economically unattractive and potentially hazardous, is necessary. (Olah et al., *Synthesis* 662 (1980)).

Other means by which an oxidative Nef reaction may be achieved include the use of potassium permanganate, ammonium/sodium persulfate, or t-butylhydroperoxide with VO(AcAc)$_2$. However each of these suffers from several drawbacks. Potassium permanganate has low solubility and its use produces large amounts of manganese dioxide as a by-product which makes product isolation difficult. (Reid et al., *Tertahedron Lett.* 31:1093 (1990); Schechter et al., *J. Org. Chem.* 27:3699 (1962)). An oxidative reaction using ammonium/sodium persulfate not only requires a large amount of the reagent but is quite sluggish and does not go to completion. (Pagano et al., *J. Org. Chem.*, 35:295 (1970)). The use of t-butylhydroperoxide with VO(AcAc)$_2$ gives very poor yields. (Bartlett et al., *Tertahedron Lett.* 4:331 (1977)).

Accordingly, there exists a need in the art for an efficient and cost-effective process for preparing aromatic ketones.

SUMMARY OF THE INVENTION

The invention provides a straightforward, efficient and cost-effective process for the oxidation of a nitro functional group of an organic compound to a carbonyl functional group on the organic compound in the presence of a catalyst.

The invention also provides a straightforward, efficient and cost-effective process for the oxidation of nitro functional organic compound having the following general formula (I):

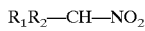
(I)

The invention also provides a straightforward, efficient and cost-effective process for the oxidation of a nitroalkyl arene compound to an aromatic ketone in the presence of a catalyst.

The invention further provides a straightforward, efficient and cost-effective process for the oxidation a nitroalkyl nitroarene compound of the general formula (III):

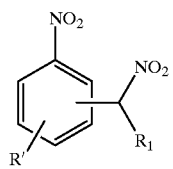
(III)

DETAILED DESCRIPTION OF THE INVENTION

One embodiment of the invention is a process for the oxidation of a nitro functional group of an organic compound to a carbonyl functional group on the organic compound in the presence of a catalyst. This process, along with preferred embodiments, is described in more detail in the following discussion and examples.

The process involves oxidizing, via a catalyzed oxidative Nef reaction, an organic compound having a nitro functional group, such as, for example, an organic compound of the formula (I):

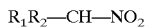
(I)

In formula (I), R$_1$ and R$_2$ are, independently, hydrogen, a substituted or unsubstituted C$_1$–C$_{10}$ alkyl, C$_6$–C$_{10}$ aryl or C$_4$–C$_{10}$ heteroaryl group or R$_1$ and R$_2$ together form a substituted or unsubstituted C$_3$–C$_7$ cycloalkyl group. The alkyl group may be straight chain or branched. Preferably, the alkyl group is a methyl, ethyl, propyl or hexyl group. Preferably the cycloalkyl group is a cyclohexyl group. Preferably, the aryl or heteroaryl group is a phenyl, furanyl, pyrrolyl, isopyrrolyl, thienyl, napthyl, pyridinyl, pyranyl, or benzyl group. The alkyl, cycloalkyl, aryl and heteroaryl group, each as described above, may be substituted or unsubstituted. Suitable substituents include alkyl, aryl, heteroaryl, ether, thioether, halo, nitro, and other similar groups. Preferably, at least one of R$_1$ and R$_2$ is a hydrogen and the other is a methyl, ethyl or hexyl group. According to the invention, an organic compound of the formula (I) may not be nitrohexane.

Upon oxidation of an organic compound of formula (I), HNO$_2$ is in effect lost. Accordingly, depending upon R$_1$ and R$_2$, oxidation of an organic compound of formula (I) may produce either an aldehyde or a ketone. Further oxidation of the aldehyde to the corresponding carboxylic acid may also be possible.

The oxidative Nef reaction may be conducted in a single phase aqueous alkaline solution system or in a single phase aqueous alkaline solution and water-miscible organic solvent system. Alternatively, the oxidative Nef reaction may be conducted in a biphasic system of an aqueous alkaline solution and a water-immiscible organic solvent. Preferably the oxidative Nef reaction is conducted is a biphasic system of an aqueous alkaline solution and a water-immiscible organic solvent.

The aqueous alkaline solution may be an aqueous solution of an alkali or alkaline earth metal carbonate or bicarbonate. Such a solution may be formed in situ. Preferably, the aqueous alkaline solution is an aqueous solution of Potassium Sodium carbonate (KNaCO$_3$). More preferably, the aqueous alkaline solution is an aqueous solution of potassium carbonate and/or potassium bicarbonate, most preferably, potassium carbonate. After completion of oxidation of an organic compound of formula (I) as described above, the aqueous alkaline solution may be recycled for use in a subsequent oxidative Nef reaction. Recycling less than the entire aqueous alkaline solution is preferred for handling purposes and to avoid substantially increasing the overall reaction volume. Preferably about 60–75% of the aqueous alkaline solution is recycled. To regenerate the alkali or alkaline earth metal carbonate, an alkali or alkaline earth metal hydroxide may be added to the recycled solution. Fresh alkali or alkaline earth metal carbonate or bicarbonate may also be added as necessary to increase the amount of alkali or alkaline earth metal carbonate or bicarbonate to the desired level. If desired, additional amounts of catalyst, as described below, may be added.

Examples of suitable water-miscible organic solvents include, but are not limited to, acetone, dimethylsulfoxide (DMSO), tetrahydrofuran (THF), N-methyl pyrrolidone (NMP), dimethylformamide (DMF) and the like. Mixtures of these solvents may also be used. In the event that DMSO is used, the catalyst, as described below, may not be one or a mixture of the following: Mn(II), Mn(VII), Co(II), and tetrabutylammonium bromide (TBAB). Examples of suitable water-immiscible organic solvent include, but are not limited to, toluene, chlorobenzene, heptane and mixtures of such solvents. Preferably the water-immiscible organic solvent is toluene. Preferably, the organic solvent is the solvent used to obtain and/or isolate the nitro compound (I).

The oxidation may be accomplished using any oxidant or mixture of oxidants known in the art. Examples of the oxidant include, but are not limited to, hydrogen peroxide, t-butyl hydroperoxide; ammonium persulfate; oxygen; permanganates, perborates such as, for example, sodium perborate; percarbonates such as, for example, sodium percarbonate; and bleach. Preferably, the ratio of oxidant:potassium carbonate:nitro compound (I) ranges from about 1.2:1.5:1 to about 2.5:2:1. For example, a preferred ratio of hydrogen peroxide:potassium carbonate:nitro compound (I) is 1.3:1.7:1. More preferably, the ratio of hydrogen peroxide:potassium carbonate:nitro compound (I) is 1.5:2.0:1, and most preferably, the ratio is 1.7:1.8:1. As discussed below, potassium permanganate may serve as a catalyst in an oxidative Nef reaction according to the invention. When potassium permanganate is used as the catalyst, it is not also used as the oxidant. When bleach is used as an oxidant, subsequent undesired reactions may occur if other functional groups are within the nitro compound (I).

During addition of the oxidant, in particular when oxygen or a reagent that can produce oxygen is used, the amount of oxygen generated or present may be monitored using an oxygen analyzer to ensure appropriate oxygen levels for the reaction to proceed and that the oxygen levels do not get dangerously high. More preferably, once a spike in oxygen levels is registered by the oxygen analyzer, the rate of addition of the oxidant may be slowed or completely stopped. Titrating the oxygen level in this manner may be used to generally indicate completion of the reaction where the nitro compound (I) acts as a limiting reagent. Other means of monitoring reaction progress include, but are not limited to, pH, color, chromatography, and infrared spectroscopy.

The catalyst may be a single catalyst or a co-catalyst system. The catalyst may be regenerated upon completion of the oxidation step. Suitable catalysts include those which increase the rate of oxidation of the nitro compound (I) to the corresponding carbonyl compound. The corresponding carbonyl compound may be an aldehyde, a ketone or a carboxylic acid. The presence of a catalyst during the oxidative Nef reaction reduces the amount of oxidant, for example, hydrogen peroxide, necessary to effect oxidation, allows the reaction to proceed at a lower temperature than an uncatalyzed reaction, and decreases overall reaction time. Examples of catalysts for use in single catalyst systems include, but are not limited to, Cu(OAc)$_2$.H$_2$O, CuCl on Alumina, Cu$_2$O, CuCl$_2$, KMnO$_4$, MnSO$_4$.H$_2$O, MnCl$_2$.4H$_2$O, MnO$_2$, (NH$_4$)$_2$Fe(SO$_4$)$_2$.6H$_2$O, tetrabutylammonium bromide (TBAB), CoBr$_2$, CoCl$_2$.6H$_2$O, CoF$_3$, Co(OAc)$_2$.4H$_2$O, Co(NO$_3$)$_2$.6H$_2$O, CoWO$_4$.xH$_2$O, SmCo$_5$, K$_2$Cr$_2$O$_7$ and amorphous CoB$_4$O$_7$.4H$_2$O ("Cobalt Borate" which may be purchased from Chem Service of West Chester, Pa. "Cobalt Borate" may also be prepared by mixing aqueous CoCl$_2$ with a hot solution of Na$_2$B$_2$O$_7$ . 4H$_2$O (Borax) to give a pale purple precipitate (crystallization) which is then digested with hot water. The crystallization and digestion may be repeated to vary Co and B percentages). The amount of single catalyst used may generally be between 0.006–36 mmol per mole of nitro compound (I). Examples of catalysts for use in co-catalyst systems include, but are not limited to, Cu(I)Cl/NH$_4$OH, Cu(II)Acetate/cocatalyst, Co(II)Cl$_2$.6H$_2$O and Co(II)(NO$_3$)$_2$.6H$_2$O in combination with a catalyst aid, as discussed below. Tertiary co-catalyst systems may also be used in the catalyzed oxidation step. Such tertiary catalyst systems include copper (II), cobalt (II), or manganese salts.

The cocatalyst may be at least one selected from the group consisting of V$_2$O$_5$, K$_2$Cr$_2$O$_7$, KMnO$_4$, FeCl$_3$.6H$_2$O, CoCl$_2$.6H$_2$O, Ni(NO$_3$)$_2$.6H$_2$O, ZnSO$_4$.7H$_2$O, (NH$_4$)$_6$(Mo$_7$O$_2$)$_4$.4H$_2$O, AgNO$_3$, SnCl$_2$, K(SbO)C$_4$H$_6$O$_6$.3/2H$_2$O, Na$_2$WO$_4$.2H$_2$O, Pb(ClO$_4$)$_2$.3H$_2$O, and (NH4)$_2$Ce(NO$_3$)$_6$.

The catalyst aid may be at least one selected from the group consisting of Fe, Mn, Cu, sodium tetraborate decahydrate (Borax), boric acid (H3BO$_3$), tetrabutylammonium bromide (TBAB), 1,4-Diazabicyclo[2.2.2]octane (Dabco), 1,8-Diazabicyclo[5.4.0]undec-7-ene (DBU), sodium 5-sulfoisophthalic acid (SSIPA), a diester of SSIPA, lithium 5-sulfoiosphthalic acid, BzEt$_3$N$^+$Cl$^-$, Tween®, sodium dodecyl sulfate (SDS), 2,4-pentanedione, methyl tributylammonium chloride, ammonium persulfate, potassium fluoride, potassium chloride, potassium bromide, potassium iodide, thioglycerol, ascorbic acid, tetrabutyl ammonium hydroxide, Co(III)F$_3$, Co(II)Br$_2$, ammonium hydroxide, and tricaprylylmethyl ammonium chloride (ie. ALIQUAT 336 available from Aldrich Chemical Company, Milwaukee, Wis.).

The amount of catalyst species, for example, Cu(I), Cu(II), or Co(II), used is generally about 0.3 mmol per mol of nitro compound (I). The amount of cocatalyst or catalyst aid used is generally between 0.2–6 mmol per mol of nitro compound (I). Completion of the oxidation reaction may be monitored by techniques known in the art including, for example, by use of an oxygen analyzer as discussed above and by gas chromatography.

A preferred embodiment of the invention is a process for the preparation of an aromatic ketone from a nitroalkyl arene compound. For example, where R$_2$ of formula (I) is a substituted or unsubstituted aromatic or heteroaromatic group. The process involves oxidizing a nitroalkyl substituent on a nitroarene compound in the presence of a catalyst to produce an aromatic ketone. This process, along with preferred embodiments, is described in more detail in the following discussion and examples.

In a preferred embodiment of a process of the invention, a nitroalkyl nitroarene compound of formula (III):

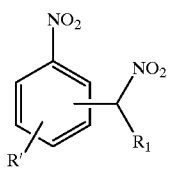

(III)

is oxidized in the presence of a catalyst to produce an aromatic ketone of formula (IV):

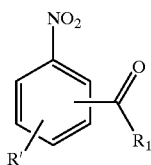

(IV)

In formulae (III) and (IV), $R_1$ is a substituted or unsubstituted $C_1$–$C_{10}$ alkyl, $C_6$–$C_{10}$ aryl or $C_4$–$C_{10}$ heteroaryl group and R' is a hydrogen or a substituted or usubstituted $C_1$–$C_{10}$ alkyl, $C_6$–$C_{10}$ aryl or $C_4$–$C_{10}$ heteroaryl group, preferably, having electron withdrawing properties. Preferably, $R_1$ is a methyl group and R' is hydrogen or an electron withdrawing group such as trifluoromethyl. When R' is an aryl group, a fused aromatic ring structure such as anthracene or naphthalene may result. In formulae (III) and (IV), respectively, the nitroalkyl group and the carbonyl group may be ortho, meta or para to the nitro group. Preferably, the nitroalkyl group and the carbonyl group are ortho to the nitro group.

Preferably, oxidation of nitroalkyl arene compound of formula (III) is achieved via a catalyzed oxidative Nef reaction to yield an aryl ketone of formula (IV). The oxidative Nef reaction may be conducted under similar conditions described above. The ratio of oxidant:potassium carbonate: nitroalkyl nitroarene compound (III) ranges from about 1.2:1.5:1 to about 2.5:2:1. For example, a preferred ratio of hydrogen peroxide:potassium carbonate: nitroalkyl nitroarene compound (III) is 1.3:1.7:1. More preferably, the ratio of hydrogen peroxide:potassium carbonate: nitroalkyl nitroarene compound (III) is 1.5:2.0:1, and most preferably, the ratio is 1.7:1.8:1. The catalyst, single and co-catalyst systems, include those described above. Again, the catalyst may be regenerated upon completion of the oxidation step. Suitable catalysts include those which increase the rate of oxidation of the nitroalkyl arene compound (III) to the aryl ketone (IV). The presence of a catalyst during the oxidative Nef reaction reduces the amount of oxidant, for example, hydrogen peroxide, necessary to effect oxidation. The amount of single or co-catalyst used is similar to the amounts described above per mole of nitroalkyl arene compound (III).

A nitroalkyl nitroarene compound of formula (III) may be prepared by contacting in the presence of an hydroxide base in a polar aprotic solvent a nitrohaloarene compound of formula

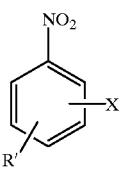

(II)

and a nitroalkane of the formula (IIa):

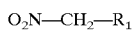

$O_2N$—$CH_2$—$R_1$ (IIa)

In formula (II), X is a halide selected from the group consisting of fluorine, chlorine, bromine and iodine and R' is as defined above. Preferably, X is chlorine or fluorine and R' is hydrogen or an electron withdrawing group such as trifluoromethyl. In formula (IIa), $R_1$ is as defined above.

Examples of suitable hydroxide bases include, but are not limited to, alkali metal hydroxides and alkaline earth metal hydroxides. Preferably, the base is the alkali metal hydroxide, such as sodium hydroxide or potassium hydroxide.

Examples of polar aprotic solvents include, but are not limited to, dimethyl sulfoxide (DMSO), N-methyl pyrrolidone (NMP), tetrahydrofuran (THF), dimethylformamide (DMF), and the like. Preferably, the polar aprotic solvent is DMSO. Mixtures of polar aprotic solvents may also be used.

Once the formation of nitroalkyl nitroarene compound of formula (III) is complete, the reaction mixture may be neutralized and the resulting nitroalkyl nitroarene compound (III) is extracted into an aromatic or aliphatic organic solvent. Examples of the organic solvent include, but are not limited to, toluene, chlorobenzene, heptane and mixtures of these solvents.

Alternatively, once the formation of nitroalkyl nitroarene compound of formula (III) is complete, a bicarbonate and water may be added to the reaction mixture. The resulting carbonate reaction mixture may then be subjected to catalyzed oxidative Nef reaction conditions described above. The bicarbonate may be an alkali or alkaline earth metal bicarbonate. Preferably the bicarbonate is sodium hydrogen carbonate or potassium hydrogen carbonate which upon reaction produces, respectively, potassium sodium carbonate ($KNaCO_3$) or potassium carbonate.

A further understanding can be obtained by reference to certain specific examples which are provided herein for purpose of illustration only and are not intended to be limiting unless otherwise specified.

EXAMPLES

Example 1

General Synthesis of 2-Nitro-4-trifluoromethylacetophenone (4) Under $KMnO_4$ Catalyzed Oxidative Nef Conditions

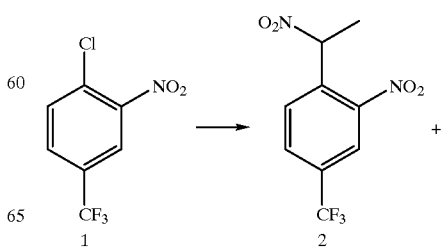

-continued

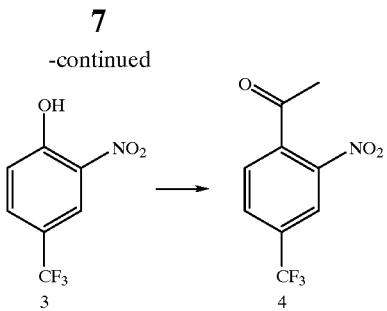

Potassium hydroxide pellets (8.42 g; 0.150 mol; 3 equiv) were crushed and placed in a 250-mL 3-necked flask equipped with a thermometer and an addition funnel. Reagent-grade DMSO (25 mL) was added and the mixture vigorously stirred. An ice-water cooling bath was then applied and when the temperature of the reaction mixture had cooled to 19° C. a mixture of nitroethane (3.95 mL; 0.055 mol; 1.1 equiv) and 4-chloro-3-nitrobenzotrifluoride (1; 7.46 mL; 0.050 mol) were added to the reaction mixture (addition funnel) over 15 min at a rate such that a temperature of 15–20° C. was maintained. After the addition was complete, the reaction mixture was cooled to 15° C. and the ice bath was replaced with a cool water bath (10–15° C.) and the reaction mixture was allowed to warm to 20° C. over 2 h, at which time GC analysis indicated >98% consumption of 1 and a ratio of 2:3 of 98:2. Toluene (25 mL) was added and the reaction mixture was cooled in ice-water. Aqueous hydrochloric acid (6 N; 15 mL; 0.090 mol) was added dropwise with vigorous stirring at such a rate that the temperature remained below 20° C. Water (40 mL) was then added and the layers were allowed to separate for 10 min. The bottom aqueous layer was decanted, and the top organic solution was used directly for the next step. An aliquot of this organic solution was analyzed by 1H NMR and indicated a 96:4 ratio of 2:3.

A solution of toluene and 2 (0.78–0.90 mol by GC analysis) was added to a solution of potassium carbonate (242.4 g; 1.75 equiv) in deionized water (642 mL) with cooling as necessary. Immediately prior to the addition of hydrogen peroxide, 0.87 mg of potassium permanganate catalyst solution in deionized water was added. Aqueous hydrogen peroxide (35%; 194 g; 2.0 equiv) was added with vigorous stirring over 2 hours while maintaining the temperature at 25° C. By the end of addition of the aqueous hydrogen peroxide, the reaction had turned orange or yellow in color. The resulting reaction mixture was stirred for 1 hour while maintaining the temperature at 24–26° C. Completion of reaction was confirmed by GC analysis. Stirring was stopped and the layers were allowed to separate. The bottom aqueous layer was removed and discarded. The organic layer was analyzed for purity by quantitative GC analysis. The nitro compound 4 was present as 23–25% of the solution to afford a 76–79% yield based on 2.

Example 2

Synthesis of 2-Nitro-4-trifluoromethylacetophenone (4) Under Cu (I) Catalyzed Oxidative Nef Conditions

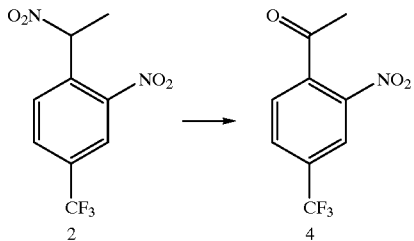

To an organic solution (74.5 g) of 2 (synthesized on a 0.1 mole scale) in toluene was added a solution of potassium carbonate (20.78 g) in deionized water (64.2 mL). A copper (I) catalyst solution (1.5 mL) of copper (I) chloride (0.05 g) and ammonium hydroxide (20 mL) was then added. Next, additional ammonium hydroxide was added (5.0 mL). Aqueous hydrogen peroxide (35%, 34.1 g) was added via an addition funnel over a 2 hour period while maintaining the temperature under 26° C. The reaction was stirred until completion as confirmed by GC analysis (approx. 1.5 hours). Stirring was stopped and layers were allowed to separate. The bottom aqueous layer was removed and discarded. The organic layer was removed to afford 64.7 g of 4 which was analyzed for purity by quantitative GC analysis and found to be 29.43%. Conversion of 1 to 4 produced an overall yield of 81.0%.

Example 3

Synthesis of 2-Nitro4-trifluoromethylacetophenone (4) Under Co (II) Catalyzed Oxidative Nef Conditions

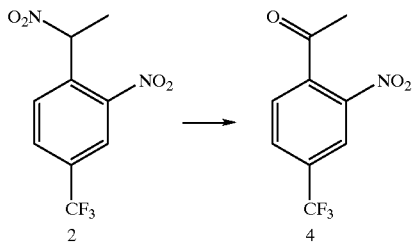

To an organic solution (35.0 g of 78.6% yield) of 2 in toluene was added a solution of potassium carbonate (12.12 g) in deionized water (33 mL). A cobalt (II) catalyst solution (2.5 mL) of cobalt (II) chloride hexahydrate (0.06 g) and water (20 mL) was then added. Aqueous hydrogen peroxide (35%, 9.7 g) was added via an addition funnel over a 1.5 hour period while maintaining the temperature under 26° C. The reaction was stirred until completion as confirmed by GC analysis (1 hour). Stirring was stopped and layers were allowed to separate. The bottom aqueous layer was removed and discarded. The organic layer afforded 30.0 g of 4 in toluene which was analyzed to be 24.6% pure by quantitative GC analysis. Conversion of 2 to 4 afforded a 80.7% yield.

Example 4

Synthesis of 2-Nitro-4-trifluoromethylacetophenone (4) Under Co (II) Catalyzed Oxidative Nef Conditions

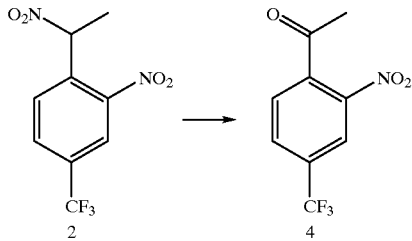

To an organic solution (35.0 g of 78.6% yield) of 2 in toluene was added a solution of potassium carbonate (12.12 g) in deionized water (33 mL). A cobalt (II) catalyst solution (2.5 mL) of cobalt (II) nitrate hexahydrate (0.07 g) and water (20 mL) was then added. Aqueous hydrogen peroxide (35%, 9.7 g) was added via an addition funnel over a 1.5 hour period while maintaining the temperature under 26° C. The reaction was stirred until completion as confirmed by GC analysis (1 hour). Stirring was stopped and layers were allowed to separate. The bottom aqueous layer was removed and discarded. The organic layer afforded 29.5 g of 4 in toluene which was analyzed to be 23.1% pure by quantitative GC analysis. Conversion of 2 to 4 afforded a 74.5% yield.

Comparative Example 1

Synthesis of 2-Nitro4-trifluoromethylacetophenone (4) in the Absence of a Catalyst

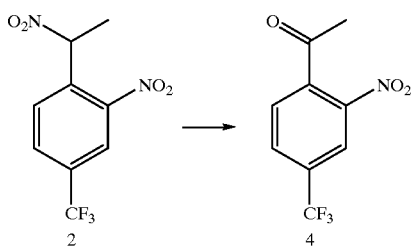

To the organic solution from Example 1 at ambient temperature (25° C.) was added a solution of potassium carbonate (13.82 g; 0.10 mol; 2 equiv) in water (15.6 mL) with vigorous stirring. Aqueous hydrogen peroxide (35%; 15.5 mL; 0.175 mol; 3.5 equiv) was added dropwise over 15 min such that the temperature was maintained below 30° C. The reaction mixture was stirred and allowed to self-heat with intermittent water bath cooling such that the temperature remained below 30° C. The reaction mixture was stirred for 17 h to completely consume 2 according to GC analysis. Acetic acid (1–2 mL) was added to afford a pH of 7–8. Stirring was stopped and the layers were allowed to separate. The bottom aqueous layer was removed and discarded, and the organic solution was washed with 1 M sodium thiosulfate (10 mL). The bottom aqueous layer was discarded, and the organic layer was removed, dried ($Na_2SO_4$), and concentrated to afford 10.51 g of 4 which was 88.85% pure by quantitative GC analysis (vs. internal standard) to afford an overall 80% yield of 4 from 1. Alternatively, the organic solution of 4 could be taken directly to the next reaction. 4: 1H NMR ($CDCl_3$) δ=8.408 (s, 1H); 8.000 (dd, 1H, J=1.47, 8.67 Hz); 7.583 (d, 1H, J=8.25 Hz); 2.600 (s, 3H). GC (30 m DB-17, 100° C., 3 min; 100–280° C., 15°/min; 280° C., 1 min): $t_R$ 8.77 min.

Example 5

Catalyzed Oxidation of Nitroethane

A mixture of toluene solution (45.5 g) containing approximately 4% or more (as determined by GC) nitroethane and aqueous potassium carbonate (12.12 g/32.1 mL water) was treated with 9.7 g of aqueous hydrogen peroxide (35%) over a 2 hour period in the presence of a catalytic amount of $KMnO_4$. Quantitative GC indicated the presence of 0.4% nitroethane and 0.8% acetaldehyde with acetic acid also being present. After another hour, quantitative GC indicated the presence of only 0.2% nitroethane, <0.8% acetaldehyde remained and up to 6% acetic acid.

Example 6

Synthesis of 2-Nitro-4-trifluoromethylacetophenone (4) Under $Co(II)Cl_2.6H_2O$/Borax Catalyzed Oxidative Nef Conditions

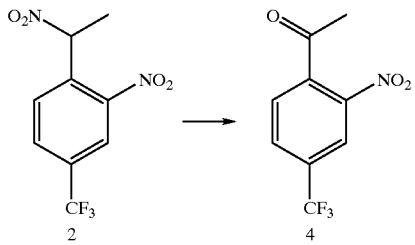

To an organic solution (140 g) of 2 (30.9% assay) in toluene in a 500 mL 3-neck round bottom flask was added a solution of potassium carbonate (47.28 g, 1.70 equivalents) in deionized water (128.4 mL). Next the reaction vessel was purged three times by pulling a vacuum on the flask and then releasing the vacuum under nitrogen. A $Co(II)Cl_2.6H_2O$/Borax catalyst solution (8.0 mL) of cobalt (II) chloride (0.106 g, 14% cobalt aqueous solution), borax (0.125 g) and water (20 mL) was then added. While maintaining the reaction temperature at 25° C. and monitoring the $O_2$ level with an $O_2$ analyzer, up to 38.8 g (2 equivalents) of aqueous hydrogen peroxide (35%) was added to the reaction mixture as follows: first, 4.7 g of aqueous hydrogen peroxide (35%) was added to the reaction mixture over a thirty minute period. Next 16.6 g of aqueous hydrogen peroxide (35%) was added to the reaction mixture over a period of an hour. A third and final addition of 17.5 g of aqueous hydrogen peroxide (35%) was begun with a target addition time of 2.5 hours. After 2.0 g of hydrogen peroxide had been added, a high oxygen level was detected. The addition was stopped, the reaction vessel was purged, and then the reaction mixture was stirred for 15 min. before addition of hydrogen peroxide was restarted. The reaction vessel was repurged if a high oxygen level was again detected by the oxygen analyzer. Once the reaction turned yellow or yellow-orange in color, addition of hydrogen peroxide (35.6 g total) was stopped. The reaction mixture (pH 9.62) was then allowed to separate into layers. The bottom aqueous layer including the oil layer was then decanted (235.2 g). The organic toluene layer containing 4 was then weighed (119.8 g, 31.58 wt % of 4, 89.8% yield). A GC trace of the organic layer indicated an area % of 4 of 100%.

Example 7

Synthesis of 2-Nitro-4-trifluoromethylacetophenone (4) Under $Co(II)Cl_2.6H_2O$/Borax Catalyzed Oxidative Nef Conditions

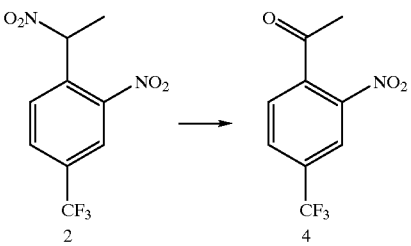

To an organic solution (140 g) of 2 (30.9% assay) in toluene was added a solution of potassium carbonate (47.28 g, 1.70 equivalents) in deionized water (128.4 mL). Next the reaction vessel was purged three times by pulling a vacuum and then releasing the vacuum under nitrogen. A Co(II) $Cl_2 \cdot 6H_2O$/Borax catalyst solution (8.0 mL) of cobalt (II) chloride (0.106 g, 14% cobalt aqueous solution), borax (0.125 g) and water (20 mL) was then added. While maintaining the reaction temperature at 25° C. and monitoring the $O_2$ level with an $O_2$ analyzer, up to 38.8 g (2 equivalents) of aqueous hydrogen peroxide (35%) was added to the reaction mixture as follows: first, 4.7 g of aqueous hydrogen peroxide (35%) was added to the reaction mixture over a thirty minute period. Next 16.6 g of aqueous hydrogen peroxide (35%) was added to the reaction mixture over a period of an hour. At the end of the second hydrogen peroxide addition, the reaction mixture was red in color. A third and final addition of 17.5 g of aqueous hydrogen peroxide (35%) was begun with a target addition time of 2.5 hours. Once the oxygen analyzer measured a high level of oxygen, addition of hydrogen peroxide (32.7 g total) was stopped, and the reaction vessel purged. GC analysis indicated the reaction was complete. The reaction mixture (pH 9.77) is then allowed to separate into layers. The bottom aqueous layer including the oil layer was then decanted (223.4 g). The organic toluene layer containing 4 was then weighed (123.1 g, 29.59 wt % of 4, 88.6% yield). A GC trace of the organic layer indicated an area % of 4 of 100%.

Example 8

General Synthesis of 2-Nitro-4-trifluoromethylacetophenone (4) Under Co(II) $Cl_2 \cdot 6H_2O$/Borax Catalyzed Oxidative Nef Conditions Using Recycled Aqueous Reaction Mixture

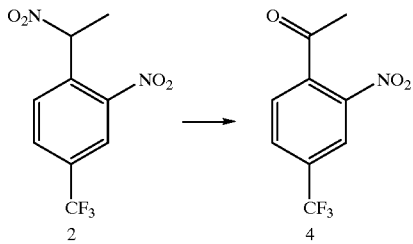

To 75% of the aqueous layer of the aqueous/oil decant of Example 7 was added potassium carbonate (2.9 g) and flake KOH to adjust pH to 11.5±0.2. Next an organic solution (35 g) of 2 (30.9% assay) in toluene was added. A Co(II) $Cl_2 \cdot 6H_2O$/Borax catalyst solution (0.125 mL) of cobalt (II) chloride hexahydrate (0.060 g), borax (0.125 g) and water (5.0 mL) was then added. While maintaining the reaction temperature at 25° C., 7.8 g (1.6 equivalents) of aqueous hydrogen peroxide (35%) was added to the reaction mixture over a 3–4 hour period. After addition of hydrogen peroxide was complete, a gas chromatography (GC) trace was taken to determine the degree of completion. If the GC indicated >98% conversion of 2 to 4, the reaction was stopped. Otherwise, the reaction mixture was then stirred at 25° C. Another GC trace was then taken every hour. The reaction mixture was then allowed to separate into layers. The bottom aqueous layer including oil and rag layers was then decanted. The organic toluene layer containing 4 was then weighed, a GC assay was performed and the yield for the reaction calculated.

Example 9

Synthesis of 2-Nitro-4-trifluoromethylacetophenone (4) Under Co(II)$Cl_2 \cdot 6H_2O$/Borax Catalyzed Oxidative Nef Conditions Using Recycled Aqueous Reaction Mixture

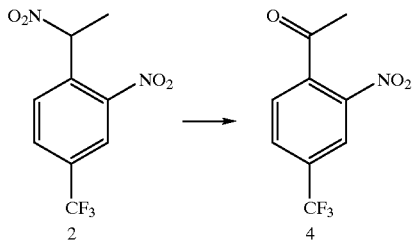

To 75% of the aqueous layer of the aqueous/oil decant (41.9 g) of Example 7 was added potassium carbonate (2.9 g) and flake KOH (0.72 g) to adjust pH to 11.58. Next an organic solution (35 g) of 2 (30.9% assay) in toluene was added. A Co(II)$Cl_2 \cdot 6H_2O$/Borax catalyst solution (0.125 mL) of cobalt (II) chloride hexahydrate (0.060 g), borax (0.125 g) and water (5.0 mL) was then added. While maintaining the reaction temperature at 25° C., 7.8 g (1.6 equivalents) of aqueous hydrogen peroxide (35%) was added to the reaction mixture over a 3–4 hour period. After addition of hydrogen peroxide was complete, a gas chromatography (GC) trace was taken to determine the degree of completion (92.7%). The reaction mixture was then stirred at 25° C. After one hour, another GC trace was taken (100%). The reaction was stopped. The reaction mixture (pH 9.26) was then allowed to separate into layers. The bottom aqueous layer including oil and rag layers was then decanted (57.6 g). The organic toluene layer containing 4 was then weighed and assayed (32.1 g, 28.4 wt % of 4, 86.6% yield).

Example 10

Synthesis of 2-Nitro-4-trifluoromethylacetophenone (4) Under Co(II)$Cl_2 \cdot 6H_2O$/Borax Catalyzed Oxidative Nef Conditions Using Recycled Aqueous Reaction Mixture

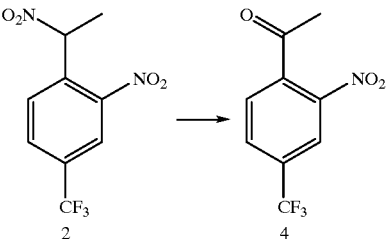

To 75% of the aqueous layer of the aqueous/oil decant (43.2 g) of Example 9 was added potassium carbonate (2.9 g) and flake KOH (3.2 g) to adjust pH to 11.6. Next an organic solution (35 g) of 2 (30.9% assay) in toluene was added. A Co(II)$Cl_2 \cdot 6H_2O$/Borax catalyst solution (0.125 mL) of cobalt (II) chloride hexahydrate (0.060 g), borax (0.125 g) and water (5.0 mL) was then added. While maintaining the reaction temperature at 25° C., 7.8 g (1.6 equivalents) of aqueous hydrogen peroxide (35%) was added to the reaction mixture over a 3–4 hour period. After addition of hydrogen peroxide was complete, a gas chromatography (GC) trace was taken to determine the degree of completion (92.4%). The reaction mixture was then stirred at 25° C. After one hour, another GC trace was taken (99.4%). The reaction was stopped. The reaction mixture (pH 9.61) was then allowed to separate into layers. The bottom aqueous layer including oil and rag layers was then decanted (69.6 g). The organic toluene layer containing 4 was then weighed and assayed (31.1 g, 29.7 wt % of 4, 87.7% yield).

Example 11

Synthesis of 2-Nitro-4-tifluoromethylacetophenone (4) Under Co(II)Cl$_2$.6H$_2$O/Borax Catalyzed Oxidative Nef Conditions Using Recycled Aqueous Reaction Mixture

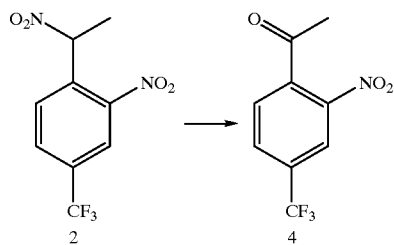

To 75% of the aqueous layer of the aqueous/oil decant (52.2 g) of Example 1 0 was added potassium carbonate (2.9 g) and flake KOH (2.2 g) to adjust pH to 11.5. Next an organic solution (35 g) of 2 (30.9% assay) in toluene was added. A CO(II)Cl$_2$.6H$_2$O/Borax catalyst solution (0.125 mL) of cobalt (II) chloride hexahydrate (0.060 g), borax (0. 125 g) and water (5.0 mL) was then added. While maintaining the reaction temperature at 25° C., 7.8 g (1.6 equivalents) of aqueous hydrogen peroxide (35%) was added to the reaction mixture over a 3–4 hour period. After addition of hydrogen peroxide was complete, a gas chromatography (GC) trace was taken to determine the degree of completion (96.5%). The reaction mixture was then stirred at 25° C. After 30 minutes, another GC trace was taken (99.6%). The reaction was stopped. The reaction mixture (pH 9.35) was then allowed to separate into layers. The bottom aqueous layer including oil and rag layers was then decanted (66.9 g). The organic toluene layer containing 4 was then weighed and assayed (31.4 g, 30.1 wt % of 4, 89.7% yield).

Example 12

Synthesis of 2-Nitro-4-trifluoromethylacetophenone (4) Under Co(II)Cl$_2$.6H$_2$O/Borax Catalyzed Oxidative Nef Conditions Using Recycled Aqueous Reaction Mixture

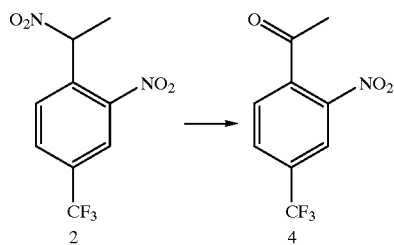

To 75% of the aqueous layer of the aqueous/oil decant (50.2 g) of Example 11 was added potassium carbonate (2.9 g) and flake KOH (2.5 g) to adjust pH to 11.5. Next an organic solution (35 g) of 2 (30.9% assay) in toluene was added. A Co(II)Cl$_2$.6H$_2$O/Borax catalyst solution (0.125 mL) of cobalt (II) chloride hexahydrate (0.060 g), borax (0 125 g) and water (5.0 mL) was then added. While maintaining the reaction temperature at 25° C., 7.8 g (1.6 equivalents) of aqueous hydrogen peroxide (35%) was added to the reaction mixture over a 3–4 hour period. After addition of hydrogen peroxide was complete, a gas chromatography (GC) trace was taken to determine the degree of completion (97.7%). The reaction mixture was then stirred at 25° C. After one hour, another GC trace was taken (98.4%). The reaction was stopped. The reaction mixture (pH 9.42) was then allowed to separate into layers. The bottom aqueous layer including oil and rag layers was then decanted (66.2 g). The organic toluene layer containing 4 was then weighed and assayed (30.8 g, 33.1 wt % of 4, 96.8% yield).

Example 13

Synthesis of 2-Nitro-4-trifluoromethylacetophenone (4) Under Co(II)Cl$_2$.6H$_2$O/Borax Catalyzed Oxidative Nef Conditions

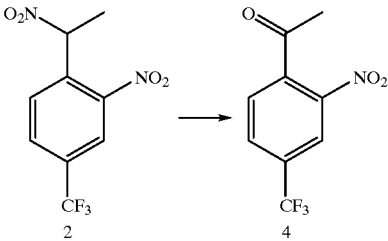

To an organic solution (35.0 g) of 2 (30.9% assay) in toluene was added a solution of potassium carbonate (11.82 g, 1.70 equivalents) in deionized water (32.1 mL). Next the reaction vessel was purged by pulling a vacuum and then releasing the vacuum under nitrogen. A Co(II)Cl$_2$.6H$_2$O/Borax catalyst solution (2.0 mL) of cobalt (II) chloride hexahydrate (0.060 g), borax (Na$_2$B$_4$O$_7$, 0.125 g) and water (20 mL) was then added. While maintaining the reaction temperature at 25° C., 9.7 g (2 equivalents) of aqueous hydrogen peroxide (35%) was added to the reaction mixture over a 3 hour period. At the end of this addition, the degree of completion of the reaction was determined by gas chromatography (GC) (93.3%). The reaction mixture was then stirred at 25° C. After one hour, another GC trace was taken (99.1%). The reaction was stopped. The reaction mixture (approx. pH 9)was then allowed to separate into layers. The bottom aqueous layer including oil and rag layers was then decanted. The organic toluene layer containing 4 was then weighed and assayed (28.84 wt % of 4, 86.6% yield).

Example 14

Synthesis of 2-Nitro-4-trifluoromethylacetophenone (4) Under Co(II)Cl$_2$.6H$_2$O/Borax Catalyzed Oxidative Nef Conditions

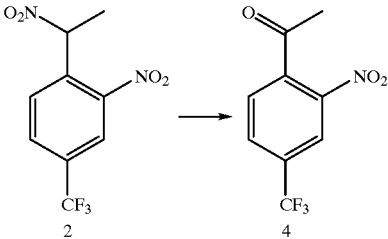

To an organic solution (35.0 g) of 2 (30.9% assay) in toluene was added a solution of potassium carbonate (11.82 g, 1.70 equivalents) in deionized water (32.1 mL). Next the reaction vessel was purged by pulling a vacuum and then releasing the vacuum under nitrogen. A Co(II)Cl$_2$.6H$_2$O/ Borax catalyst solution (2.0 mL) of cobalt (II) chloride (0.106 g, 14% cobalt aqueous solution), borax (Na$_2$B$_4$O$_7$, 0.125 g) and water (20 mL) was then added. While maintaining the reaction temperature at 25° C., 9.7 g (2 equivalents) of aqueous hydrogen peroxide (35%) was added to the reaction mixture over a 3 hour period. At the end of this addition, the degree of completion of the reaction was determined by gas chromatography (GC) (98.9%). The reaction mixture was then stirred at 25° C. After one hour, another GC trace was taken (100%). The reaction was stopped. The reaction mixture (approx. pH 9) was then allowed to separate into layers. The bottom aqueous layer including oil and rag layers was then decanted. The organic toluene layer containing 4 was then weighed and assayed (29.16 wt % of 4, 86.4% yield).

Example 15

Synthesis of 2-Nitro-4-trifluoromethylacetophenone (4) Under Co(II)Cl$_2$.6H$_2$O/tetrabutylammonium Bromide (TBAB) Catalyzed Oxidative Nef Conditions

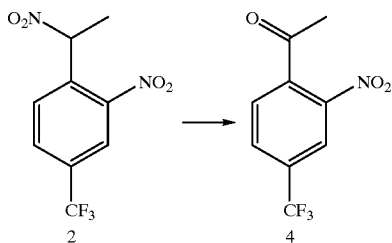

To an organic solution (140 g) of 2 (30.9% assay) in toluene was added a solution of potassium carbonate (47.28 g, 1.70 equivalents) in deionized water (128.4 mL). Next the reaction vessel was purged by pulling a vacuum and then releasing the vacuum under nitrogen. A Co(II)Cl$_2$.6H$_2$O/ TBAB catalyst solution (8.0 mL) of cobalt (II) chloride hexahydrate (0.060 g), TBAB (1.35 g, 50% aqueous solution) and water (20 mL) was then added. While maintaining the reaction temperature at 25° C., 38.8 g (2 equivalents) of aqueous hydrogen peroxide (35%) was added to the reaction mixture as follows: first, 4.7 g of aqueous hydrogen peroxide (35%) was added to the reaction mixture over a thirty minute period. Next 16.6 g of aqueous hydrogen peroxide (35%) was added to the reaction mixture over a period of an hour. At the end of hydrogen peroxide addition, the reaction mixture is red in color. A third and final addition of 17.5 g of aqueous hydrogen peroxide (35%) was begun with a target addition time of 2.5 hours. Once the oxygen analyzer indicated a high oxygen level and the reaction turned yellow or yellow-orange in color, addition of hydrogen peroxide (30.3 g total) was stopped (100% completion as indicated by GC). The reaction mixture (pH 9.66) is then allowed to separate into layers. The bottom aqueous layer including the oil layer is then decanted (225.8 g). The organic toluene layer containing 4 was then weighed (128.6 g, 29.57 wt % of 4, 90.3% yield). A GC trace of the organic layer indicated an area % of 4 of 100%.

Comparative Example 2

Synthesis of 2-Nitro-4-trifluoromethylacetophenone (4) Under Non-catalyzed Oxidative Nef Conditions

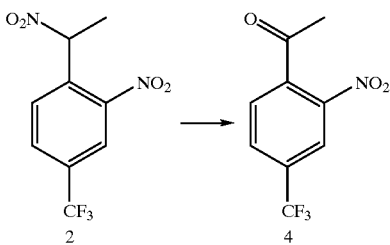

To an organic solution (140 g) of 2 (30.9% assay) in toluene was added a solution of potassium carbonate (47.28 g, 1.70 equivalents) in deionized water (128.4 mL). Next the reaction vessel was purged by pulling a vacuum and then releasing the vacuum under nitrogen several times. While maintaining the reaction temperature at 25° C., 38.8 g (2 equivalents) of aqueous hydrogen peroxide (35%) was added to the reaction mixture as follows: first, 4.7 g of aqueous hydrogen peroxide (35%) was added to the reaction mixture over a thirty minute period. The reaction mixture was dark brown in color. Next 16.6 g of aqueous hydrogen peroxide (35%) was added to the reaction mixture over a period of an hour. A third and final addition of 17.5 g of aqueous hydrogen peroxide (35%) was then added over 2.5 hours. The reaction mixture is reddish brown in color. The reaction was sampled for completion every hour and, once complete, stirred at 25° C. overnight. The reaction mixture (pH 9.63) was then allowed to separate into layers. The bottom aqueous layer including the oil layer is then decanted (226.7 g). The organic toluene layer containing 4 was then weighed (123.9 g, 29.39 wt % of 4, 86.4% yield). A GC trace of the organic layer indicated an area % of 4 of 100%.

Example 16

Synthesis of 2-Nitro-4-trifluoromethylacetophenone (4) Under Co(II)Cl$_2$.6H$_2$O/Aliquat ® 336 Catalyzed Oxidative Nef Conditions

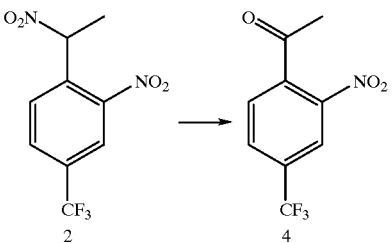

To an organic solution (140 g) of 2 in toluene was added a solution of potassium carbonate (47.28 g, 1.70 equivalents) in deionized water (128.4 mL). Next the reaction vessel was purged by pulling a vacuum and then releasing the vacuum under nitrogen several times. A Co(II) Cl$_2$.6H$_2$O/Aliquat ® 336 catalyst solution (8.0 mL) of cobalt (II) chloride hexahydrate (0.060 g), tricaprylylnethylammonium chloride (Aliquat ® 336, 0.84 g) and water (20 mL) was then added. While maintaining the reaction temperature at 25° C., up to 38.8 g (2 equivalents) of aqueous hydrogen peroxide (35%) was added to the reaction mixture as follows: first, 4.7 g of aqueous hydrogen peroxide (35%) was added to the reaction mixture over a thirty minute period.

Next 16.6 g of aqueous hydrogen peroxide (35%) was added to the reaction mixture over a period of an hour. The reaction mixture turned red/orange in color. A third and final addition of 17.5 g of aqueous hydrogen peroxide (35%) was begun with a target addition time of 2.5 hours. Once the reaction turned yellow in color, and the oxygen level rose, addition of hydrogen peroxide (35.6 g total) was stopped. The reaction mixture (pH 9.63) is then allowed to separate into layers. The bottom aqueous layer including the oil layer is then decanted (226.4 g). The organic toluene layer containing 4 was then weighed (124.4 g, 30.93 wt % of 4, 91.4% yield). A GC trace of the organic layer indicated an area % of 4 of 100%.

Example 17

Synthesis of Cyclohexanone via Catalyzed Oxidative Nef Reaction of Nitrocyclohexane Potassium carbonate (3.0 g) was dissolved in deionized water (8 mL) in a beaker and transferred to a 250 mL reaction vessel. Next Cobalt Borate catalyst (0.5 mL, 0.060 g Co/0.125 g Borax in 20 mL deionized water) was added. Nitrocyclohexane (1.53 g) was then added. While maintaining the temperature at 25° C., 2.4 g of aqueous hydrogen peroxide (35%) was added to the reaction mixture over a 2 hour period. At the end of this addition, no color change was observed and gas chromatography (GC) indicated no oxidation product. The reaction was then stirred at 25° C. and a GC trace was taken after one hour and then again after two hours, both traces indicated no oxidation product. An additional 2.4 g of aqueous hydrogen peroxide (35%) was added to the reaction mixture and the resulting reaction mixture was stirred at 25° C. After one hour, another GC trace was taken and indicated little to no oxidation product. The reaction was stirred at 25° C. for approximately 36 hours. GC trace indicated the production of cyclohexanone (ca. 13,8 area %, 14% conversion).

Example 18

Synthesis of p-Nitroacetophenone (6)

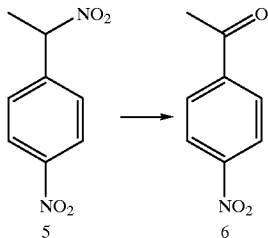

To an organic solution (27.2 g) of 5 in toluene was added a solution of potassium carbonate (12.12 g) in deionized water (32.1 mL). A $KMnO_4$ catalyst solution (0.5 mL) of potassium permanganate (0.029 g) in deionized water (100 mL) was then added. Next, 9.7 g of aqueous hydrogen peroxide (35%) was added over a 2 hour period while maintaining the temperature at 25° C. Once addition of hydrogen peroxide was complete, the reaction was stirred until completion as confirmed by GC analysis (approx. 2.0 hours). Stirring was stopped and layers were allowed to separate. The bottom aqueous layer was removed and discarded and 23.6 g of the organic layer containing 6 was recovered.

The claimed invention is:

1. A process for preparing a carbonyl compound comprising the step of:

oxidizing, in the presence of a catalyst, a nitro functional group of an organic compound to a carbonyl functional group on the organic compound, wherein said oxidizing step is conducted in a single phase aqueous alkaline solution system, a single phase aqueous and water-miscible organic solvent system or a biphasic aqueous alkaline solution and a water-immiscible organic solvent system.

2. A process of claim 1, wherein said nitro functional organic compound has the following formula (I):

where $R_1$ and $R_2$ are, independently, a hydrogen, a substituted or unsubstituted $C_1–C_{10}$ alkyl, $C_6–C_{10}$ aryl or $C_4–C_{10}$ heteroaryl group or $R_1$ and $R_2$ together form a substituted or unsubstituted $C_3–C_7$ cycloalkyl group with the proviso that the organic compound of formula (I) is not nitrohexane.

3. A process of claim 2, wherein $R_1$ is a hydrogen and $R_2$ is a substituted or unsubstituted methyl, ethyl, hexyl, cyclohexyl, phenyl, furanyl, pyrrolyl, isopyrrolyl, thienyl, napthyl, pyridinyl, pyranyl, or benzyl group.

4. A process of claim 1, wherein said carbonyl functional group is a ketone, an aldehyde, or a carboxylic acid.

5. A process of claim 4, wherein said organic compound is a ketone.

6. A process of claim 1, wherein said aqueous alkaline solution is an aqueous solution of an alkali or alkaline earth metal carbonate or bicarbonate.

7. A process of claim 6, wherein said alkali or alkaline earth metal carbonate is a potassium carbonate and said oxidizing step is conducted in a biphasic aqueous alkaline solution and a water-immiscible organic solvent system.

8. A process of claims 7, wherein said water-immiscible organic solvent is toluene.

9. A process of claim 1, wherein said oxidizing step comprises the step of adding an oxidant selected from the group consisting of hydrogen peroxide, t-butyl hydroperoxide, ammonium persulfate, oxygen, permanganate, perborate, percarbonate, and bleach.

10. A process of claim 9, wherein said oxidant is hydrogen peroxide.

11. A process of claim 1, wherein said catalyst is a single catalyst selected from the group consisting of $Cu(OAc)_2.H_2O$, CuCl on Alumina, $Cu_2O$, $CuCl_2$, $KMnO_4$, $MnSO_4.H_2O$, $MnCl_2.4H_2O$, $MnO_2$, $(NH_4)_2Fe(SO_4)_2.6H_2O$, tetrabutylammonium bromide (TBAB), $CoBr_2$, $CoCl_2.6H_2O$, $CoF_3$, $Co(OAc)_2.4H_2O$, $Co(NO_3)_2.6H_2O$, $CoWO_4.H_2O$, $SmCo_5$, $K_2Cr_2O_7$ and amorphous $CoB_4O_7$ $4H_2O$; or a co-catalyst selected from the group consisting of $Cu(I)Cl/NH_4OH$, Cu(II)Acetate/cocatalyst, $Co(II)Cl_2.6H_2O$ and $Co(II)(NO_3)_2.6H^2O$ in combination with a catalyst aid.

12. A process of claim 11, wherein said cocatalyst is at least one selected from the group consisting of $V_2O_5$, $K_2Cr_2O_7$, $KMnO_4$, $FeCl_3.6H_2O$, $CoCl_2.6H_2O$, $Ni(NO_3)_2.6H_2O$, $ZnSO_4.7H_2O$, $(NH_4)_6(Mo_7O_2)_4.4H_2O$, $AgNO_3$, $SnCl_2$, $K(SbO)C_4H_6O_6.3/2H_2O$, $Na_2WO_4.2H_2O$, $Pb(ClO_4)_2.3H_2O$, and $(NH4)_2Ce(NO_3)_6$; and said catalyst aid is at least one selected from the group consisting of Fe, Mn, Cu, sodium tetraborate decahydrate (Borax), boric acid ($H_3BO_3$), tetrabutylammonium bromide (TBAB), 1,4-Diazabicyclo[2.2.2]octane (Dabco), 1,8-Diazabicyclo[5.4.0]undec-7-ene (DBU), sodium 5-sulfoisophthalic acid (SSIPA), a diester of SSIPA, lithium 5-sulfoiosphthalic acid, $BzEt_3N^+Cl^{31}$, Polyoxyethylene (20) sorbitan monooleate, sodium dodecyl sulfate (SDS), 2,4-pentanedione, methyl tributylammonium chloride, ammonium persulfate, potassium fluoride, potassium chloride, potassium bromide, potassium iodide, thioglycerol, ascorbic acid, tetrabutyl ammonium hydroxide, $Co(III)F_3$, $Co(II)Br_2$, ammonium hydroxide, and tricaprylylmethyl ammonium chloride.

13. A process for preparing an aromatic ketone comprising the step of:
   oxidizing, in the presence of a catalyst, a nitoalky arene compound under conditions sufficient to produce an aromatic ketone.

14. A process of claim 13, wherein said nitroalkyl arene compound is a nitroalkyl nitroarene compound of the formula (III):

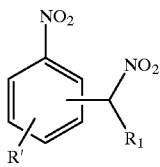

(III)

where $R_1$ is a substituted or unsubstituted $C_1$–$C_{10}$ alkyl, $C_6$–$C_{10}$ aryl or $C_4$–$C_{10}$ heteroaryl group; and R' is a hydrogen, an electron withdrawing substituted or unsubstituted $C_1$–$C_{10}$ alkyl, $C_6$–$C_{10}$ aryl or $C_4$–$C_{10}$ heteroaryl group, or, when taken together with the phenyl ring of (III), a fused aromatic ring structure; and said aromatic ketone has the formula (IV):

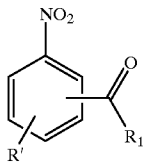

(IV)

where $R_1$ is a substituted or unsubstituted $C_1$–$C_{10}$ alkyl, $C_6$–$C_{10}$ aryl or $C_4$–$C_{10}$ heteroaryl group; and R' is a hydrogen, an electron withdrawing substituted or unsubstituted $C_1$–$C_{10}$ alkyl, $C_6$–$C_{10}$ aryl or $C_4$–$C_{10}$ heteroaryl group, or, when taken together with the phenyl ring of (III), a fused aromatic ring structure.

15. A process of claim 14, wherein $R_1$ is a methyl group and R' is a hydrogen or a trifluoromethyl group.

16. A process of claim 13, wherein said oxidizing step is conducted in a single phase aqueous alkaline solution system, a single phase aqueous and water-miscible organic solvent system, or a biphasic aqueous alkaline solution and a water-immiscible organic solvent system.

17. A process of claim 13, wherein said aqueous alkaline solution is an aqueous solution of an alkali or alkaline earth metal carbonate or bicarbonate.

18. A process of claim 17, wherein said alkali or alkaline earth metal carbonate is a potassium carbonate and said oxidizing step is conducted in a biphasic aqueous alkaline solution and a water-immiscible organic solvent system.

19. A process of claim 18, wherein said water-immiscible organic solvent is toluene.

20. A process of claim 13, wherein said oxidizing step comprises the step of adding an oxidant selected from the group consisting of hydrogen peroxide, t-butyl hydroperoxide, ammonium persulfate, oxygen, permanganate, perborate, percarbonate, and bleach.

21. A process of claim 20, wherein said oxidant is hydrogen peroxide.

22. A process of claim 13, wherein said catalyst is a single catalyst selected from the group consisting of $Cu(OAc)_2 \cdot H_2O$, CuCl on Alumina, $Cu_2O$, $CuCl_2$, $KMnO_4$, $MnSO_4 \cdot H_2O$, $MnCl_2 \cdot 4H_2O$, $MnO_2$, $(NH_4)_2Fe(SO_4)_2 \cdot 6H_2O$, tetrabutylammonium bromide (TBAB), $CoBr_2$, $CoCl_2 \cdot 6H_2O$, $CoF_3$, $Co(OAc)_2 \cdot 4H_2O$, $Co(NO_3)_2 \cdot 6H_2O$, $CoWO_4 \cdot xH_2O$, $SmCo_5$, $K_2Cr_2O_7$ and amorphous $CoB_4O_7 \cdot 4H_2O$; or a co-catalyst selected from the group consisting of $Cu(I)Cl/NH_4OH$, Cu(II)Acetate/cocatalyst, $Co(II)Cl_2 \cdot 6H2O$ and $Co(II)(NO3)_2 \cdot 6H_2O$ in combination with a catalyst aid.

23. A process of claim 22, wherein said cocatalyst is at least one selected from the group consisting of $V_2O_5$, $K_2Cr_2O_7$, $KMnO_4$, $FeCl_3 \cdot 6H_2O$, $CoCl_2 \cdot 6H_2O$, $Ni(NO_3)_2 \cdot 6H_2O$, $ZnSO_4 \cdot 7H_2O$, $(NH_4)_6(Mo_7O_2)_4 \cdot 4H_2O$, $AgNO_3$, $SnCl_2$, $K(SbO)C_4H_6O_6 \cdot 3/2H_2O$, $Na_2WO_4 \cdot 2H_2O$, $Pb(ClO_4)_2 \cdot 3H_2O$, and $(NH_4)_2Ce(NO_3)_6$; and said catalyst aid is at least one selected from the group consisting of Fe, Mn, Cu, sodium tetraborate decahydrate (Borax), boric acid ($H_3BO_3$), tetrabutylammonium bromide (TBAB), 1,4-Diazabicyclo[2.2.2]octane (Dabco), 1,8-Diazabicyclo[5.4.0]undec-7-ene (DBU), sodium 5-sulfoisophthalic acid (SSIPA), a diester of SSIPA, lithium 5-sulfoiosphthalic acid, $BzEt_3N^+Cl^-$, Polyoxyethylene (20) sorbitan monooleate sodium dodecyl sulfate (SDS), 2,4-pentanedione, methyl tributylammonium chloride, ammonium persulfate, potassium fluoride, potassium chloride, potassium bromide, potassium iodide, thioglycerol, ascorbic acid, tetrabutyl ammonium hydroxide, $Co(III)F_3$, $Co(II)Br_2$, ammonium hydroxide, and tricaprylylmethyl ammonium chloride.

* * * * *